(12) United States Patent
Kim et al.

(10) Patent No.: US 11,004,134 B2
(45) Date of Patent: May 11, 2021

(54) METHOD AND SYSTEM FOR PROVIDING FACE-BASED SERVICES AND NON-TRANSITORY COMPUTER-READABLE RECORDING MEDIUM

(71) Applicant: MORPHEUS CO., LTD., Gyeonggi-do (KR)

(72) Inventors: Jin Su Kim, Seoul (KR); Heung San Choi, Seoul (KR)

(73) Assignee: MORPHEUS CO., LTD., Seongnam-si (KR)

( * ) Notice: Subject to any disclaimer, the term of this patent is extended or adjusted under 35 U.S.C. 154(b) by 491 days.

(21) Appl. No.: 15/541,512

(22) PCT Filed: Mar. 13, 2015

(86) PCT No.: PCT/KR2015/002436
§ 371 (c)(1),
(2) Date: Jul. 5, 2017

(87) PCT Pub. No.: WO2016/111415
PCT Pub. Date: Jul. 14, 2016

(65) Prior Publication Data
US 2018/0018728 A1    Jan. 18, 2018

(30) Foreign Application Priority Data

Jan. 5, 2015  (KR) .................. 10-2015-0000699

(51) Int. Cl.
*G06Q 30/06*  (2012.01)
*G06K 9/00*  (2006.01)
(Continued)

(52) U.S. Cl.
CPC ..... *G06Q 30/0631* (2013.01); *G06K 9/00255* (2013.01); *G06K 9/00288* (2013.01);
(Continued)

(58) Field of Classification Search
CPC ........... G06Q 30/0631; G06Q 30/0613; G06Q 30/0643; G06Q 50/22; G06K 9/00255;
(Continued)

(56) References Cited

U.S. PATENT DOCUMENTS 6,293,284 B1 * 9/2001 Rigg .................... A45D 44/005
132/200
7,079,158 B2 * 7/2006 Lambertsen ......... A45D 44/005
345/592
(Continued)

FOREIGN PATENT DOCUMENTS

| JP | 2004-005401 A | 1/2004 |
| KR | 10-2005-0043180 A | 5/2005 |
| KR | 10-2013-0139521 A | 12/2013 |

OTHER PUBLICATIONS

Sajjad, Asma, et al. "Virtual Makeover Software." International Journal of Computer Applications 975 (2013): 8887. (Year: 2013).*
(Continued)

*Primary Examiner* — Asfand M Sheikh
(74) *Attorney, Agent, or Firm* — Dinsmore & Shohl LLP; Yongsok Choi, Esq.

(57) ABSTRACT

According to one aspect of the present invention, provided is a method for providing face-based services, comprising the steps of: (a) collecting, for at least one user, face-related data including face data; (b) determining a service provider matching the face-related data of a first user who wants to receive the service, by using a service provider introduction algorithm; (c) transmitting the face-related data of the first user to a server of the service provider; and (d) receiving, from the server of the service provider, the face-related data which is changed or newly generated by the service provided to the first user from the service provider, wherein information related to data processed in at least one step of steps (a), (b), (c) and (d) or information related to operations (Continued)

performed in at least one step of steps (a), (b), (c) and (d) is provided to a terminal device of the first user.

20 Claims, 4 Drawing Sheets

(51) Int. Cl.
*G06T 13/40* (2011.01)
*G06Q 50/22* (2018.01)

(52) U.S. Cl.
CPC ......... *G06T 13/40* (2013.01); *G06Q 30/0643* (2013.01); *G06Q 50/22* (2013.01)

(58) Field of Classification Search
CPC . G06K 9/00288; G06K 9/00302; G06T 13/40
See application file for complete search history.

(56) References Cited

U.S. PATENT DOCUMENTS

| | | | | |
|---|---|---|---|---|
| 8,498,456 B2 * | 7/2013 | Legagneur | A45D 44/005 | 382/118 |
| 8,555,164 B2 * | 10/2013 | Huang | G06T 13/40 | 715/706 |
| 8,693,768 B1 * | 4/2014 | LaForgia | A45D 44/005 | 222/1 |
| 10,553,006 B2 * | 2/2020 | Iglehart | G06K 9/00221 | |
| 2002/0024528 A1 * | 2/2002 | Lambertsen | A45D 44/005 | 345/646 |
| 2002/0094074 A1 * | 7/2002 | Lurie | G06Q 10/06315 | 379/221.02 |
| 2003/0065524 A1 * | 4/2003 | Giacchetti | A45D 44/005 | 700/49 |
| 2004/0110113 A1 * | 6/2004 | Huang | G09B 19/00 | 434/100 |
| 2005/0147955 A1 * | 7/2005 | Giacchetti | G06Q 50/22 | 434/377 |
| 2005/0267778 A1 * | 12/2005 | Kazman | G06Q 30/0601 | 705/26.1 |
| 2007/0067225 A1 * | 3/2007 | Fabris | G06Q 10/02 | 705/26.41 |
| 2009/0234716 A1 * | 9/2009 | Mallick | G06F 3/0482 | 705/14.54 |
| 2013/0066750 A1 * | 3/2013 | Siddique | G06Q 10/0637 | 705/27.2 |
| 2014/0236935 A1 * | 8/2014 | Doebele | G06Q 50/01 | 707/723 |
| 2014/0279192 A1 * | 9/2014 | Selby | G06Q 30/0631 | 705/26.7 |
| 2014/0351092 A1 * | 11/2014 | Burkhart | G06Q 30/0282 | 705/26.62 |
| 2015/0250294 A1 * | 9/2015 | Miller | A45D 44/005 | 434/100 |
| 2015/0346936 A1 * | 12/2015 | Rodan | H04L 67/10 | 715/745 |
| 2017/0046634 A1 * | 2/2017 | Terzian | G06F 16/958 | |

OTHER PUBLICATIONS

International Search Report pertaining to PCT/KR2015/002436 dated Aug. 31, 2015.

* cited by examiner

METHOD AND SYSTEM FOR PROVIDING FACE-BASED SERVICES AND NON-TRANSITORY COMPUTER-READABLE RECORDING MEDIUM

FIELD OF THE INVENTION

The present invention relates to a method, system, and non-transitory computer-readable recording medium for providing face-based services.

BACKGROUND

Growing interest in appearances is increasing interest in services and products that assist in decorating appearances, such as cosmetic surgery, dermatologic treatment, cosmetics, and accessories. Traditionally, such services and products have been offered individually through small business entities. The small business entities have been forced to perform reactive marketing rather than proactive marketing, and to provide the services and products according to circumstances. In recent years, as demand for the services and products that assist in decorating appearances has increased explosively, problems and limitations are being revealed in providing the services and products in conventional manners.

Particularly, as for medical services such as cosmetic surgery, although the size of domestic cosmetic surgery market amounts to about 5 trillion won, the manners of providing services related to cosmetic surgery are still traditional and causing many problems. For example, there are frequent cases where a patient undergoes cosmetic surgery only depending on promotion or explanation from a hospital and fails to get a satisfactory surgical result, or where a broker who mediates cosmetic surgery between a patient and a hospital conducts improper mediation solely for his/her economic benefit, so that the patient suffers economic or mental damage.

Since cosmetic surgery is basically medical practice, patients receive services in a state where they do not have enough information compared to hospitals (or brokers as mentioned above), and such information imbalance causes a lot of problems. Particularly, there are cases where foreigners visiting Korea for cosmetic surgery suffer significant damage due to linguistic barriers and ignorance about domestic circumstances.

SUMMARY OF THE INVENTION

One object of the present invention is to solve all the above-described problems in the prior art.

Another object of the invention is to allow a user to receive face-based services suitable for face-related data of the user, and to transparently receive related information while receiving the services, by collecting face-related data including face data generated by a face data generation device, with respect to at least one user; determining a service provider matched with the face-related data of a first user desiring to receive services, using a service provider commission algorithm; transmitting the face-related data of the first user to a server of the determined service provider; receiving, from the server of the service provider, the face-related data changed or newly generated by the services provided from the service provider to the first user; and providing information on data processed or operations performed in the above procedures to a terminal device of the first user.

The representative configurations of the invention to achieve the above objects are described below.

According to one aspect of the invention, there is provided a method for providing face-based services, comprising the steps of: (a) collecting face-related data including face data with respect to at least one user; (b) determining a service provider matched with the face-related data of a first user desiring to receive services, using a service provider commission algorithm; (c) transmitting the face-related data of the first user to a server of the determined service provider; and (d) receiving, from the server of the determined service provider, the face-related data changed or newly generated by the services provided from the service provider to the first user, wherein information on data processed in at least one of steps (a), (b), (c) and (d), or information on operations performed in at least one of steps (a), (b), (c) and (d), is provided to a terminal device of the first user.

According to another aspect of the invention, there is provided a system for providing face-based services, comprising: a face data collection unit configured to collect face-related data including face data with respect to at least one user; a service provider management unit configured to determine a service provider matched with the face-related data of a first user desiring to receive services, using a service provider commission algorithm, to transmit the face-related data of the first user to a server of the determined service provider, and to receive, from the server of the determined service provider, the face-related data changed or newly generated by the services provided from the service provider to the first user; and an application management unit configured to provide information on data processed by the face data collection unit and the service provider management unit, or information on operations performed by the face data collection unit and the service provider management unit, to a terminal device of the first user.

In addition, there are further provided other methods and systems to implement the invention, as well as non-transitory computer-readable recording media having stored thereon computer programs for executing the methods.

According to the invention, a user desiring to receive services may receive services suitable for face-related data of the user, and may transparently receive related information while receiving the services.

According to the invention, a service provider providing face-based services may accurately recognize conditions or needs of users.

According to the invention, communication (i.e., information exchange) may be smoothly performed between users and service providers.

DETAILED DESCRIPTION

In the following detailed description of the present invention, references are made to the accompanying drawings that show, by way of illustration, specific embodiments in which the invention may be practiced. These embodiments are described in sufficient detail to enable those skilled in the art to practice the invention. It is to be understood that the various embodiments of the invention, although different from each other, are not necessarily mutually exclusive. For example, specific shapes, structures and characteristics described herein may be implemented as modified from one embodiment to another without departing from the spirit and scope of the invention. Furthermore, it shall be understood that the locations or arrangements of individual elements within each of the embodiments may also be modified without departing from the spirit and scope of the invention. Therefore, the following detailed description is not to be taken in a limiting sense, and the scope of the invention is to be taken as encompassing the scope of the appended claims and all equivalents thereof. In the drawings, like reference numerals refer to the same or similar elements throughout the several views.

Hereinafter, various preferred embodiments of the present invention will be described in detail with reference to the accompanying drawings to enable those skilled in the art to easily implement the invention.

Configuration of an Entire System

Figure 1:
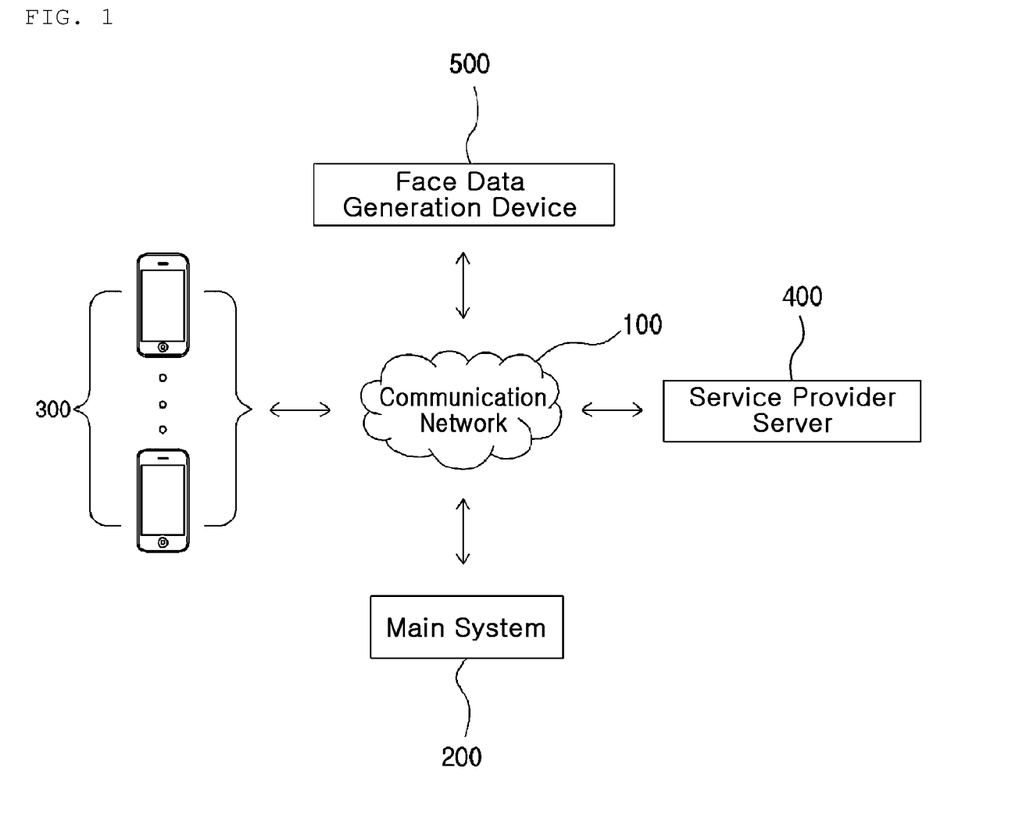
FIG. 1 schematically shows the configuration of an entire system for providing face-based services according to one embodiment of the invention.

FIG. 1 schematically shows the configuration of an entire system for providing face-based services according to one embodiment of the invention.

As shown in FIG. 1, the entire system according to one embodiment of the invention may comprise a communication network 100, a main system 200, a user terminal device 300, a service provider server 400, and a face data generation device 500.

First, the communication network 100 according to one embodiment of the invention may be implemented regardless of communication modality such as wired and wireless communications, and may be constructed from a variety of communication networks such as local area networks (LANs), metropolitan area networks (MANs), and wide area networks (WANs). Preferably, the communication network 100 described herein may be the Internet or the World Wide Web (WWW). However, the communication network 100 is not necessarily limited thereto, and may at least partially include known wired/wireless data communication networks, known telephone networks, or known wired/wireless television communication networks.

Next, the main system 200 according to one embodiment of the invention may function to, in cooperation with the user terminal device 300, the service provider server 400, or the face data generation device 500 over the communication network 100, collect face-related data including face data generated by the face data generation device 500, with respect to at least one user; determine a service provider matched with the face-related data of a first user, using a service provider commission algorithm; transmit the face-related data of the first user to the server 400 of the determined service provider; receive, from the server 400 of the service provider, the face-related data changed or newly generated by the services provided from the service provider to the first user; and provide information on data processed or operations performed in the above procedures to the terminal device 300 of the first user, thereby allowing a user to receive face-based services suitable for face-related data of the user, and to transparently receive related information while receiving the services.

The configuration and function of the main system 200 according to the invention will be discussed in more detail below.

Next, the user terminal device 300 according to one embodiment of the invention is digital equipment that may function to allow a user to connect to and then communicate with the main system 200, the service provider server 400, or the face data generation device 500, and any type of digital equipment having a memory means and a microprocessor for computing capabilities, such as a smart phone, a tablet, and a personal (desktop or laptop) computer may be adopted as the user terminal device 300 according to the invention.

Meanwhile, according to one embodiment of the invention, an application for assisting a user to receive services according to the invention may be installed in the user terminal device 300. The configuration and function of the application installed in the user terminal device 300 will be discussed in more detail below.

Next, the service provider server 400 according to one embodiment of the invention is digital equipment that may function to allow a service provider to connect to and then communicate with the main system 200, the user terminal device 300, or the face data generation device 500, and any type of digital equipment having a memory means and a microprocessor for computing capabilities, such as a smart phone, a tablet, a personal (desktop or laptop) computer, and a workstation may be adopted as the service provider server 400 according to the invention. For example, the service provider server 400 according to one embodiment of the invention may be a server operated by a hospital, a dealer in cosmetics, or a dealer in accessories such as eyeglasses.

Next, the face data generation device 500 according to one embodiment of the invention is digital equipment that may function to connect to and then communicate with the main system 200, the user terminal device 300, or the service provider server 400, and may function to generate face data of a user by directly scanning or photographing the user's face. According to one embodiment of the invention, the face data generation device 500 may include a facial bone scanning device, a facial image photographing device, or the like. According to one embodiment of the invention, the face data generation device 500 may be disposed at a place where users may easily visit (e.g., a concierge center), and also at a facility or store (e.g. a hospital, a cosmetics store, etc.) operated by a service provider.

Configuration of the Main System

Figure 2:
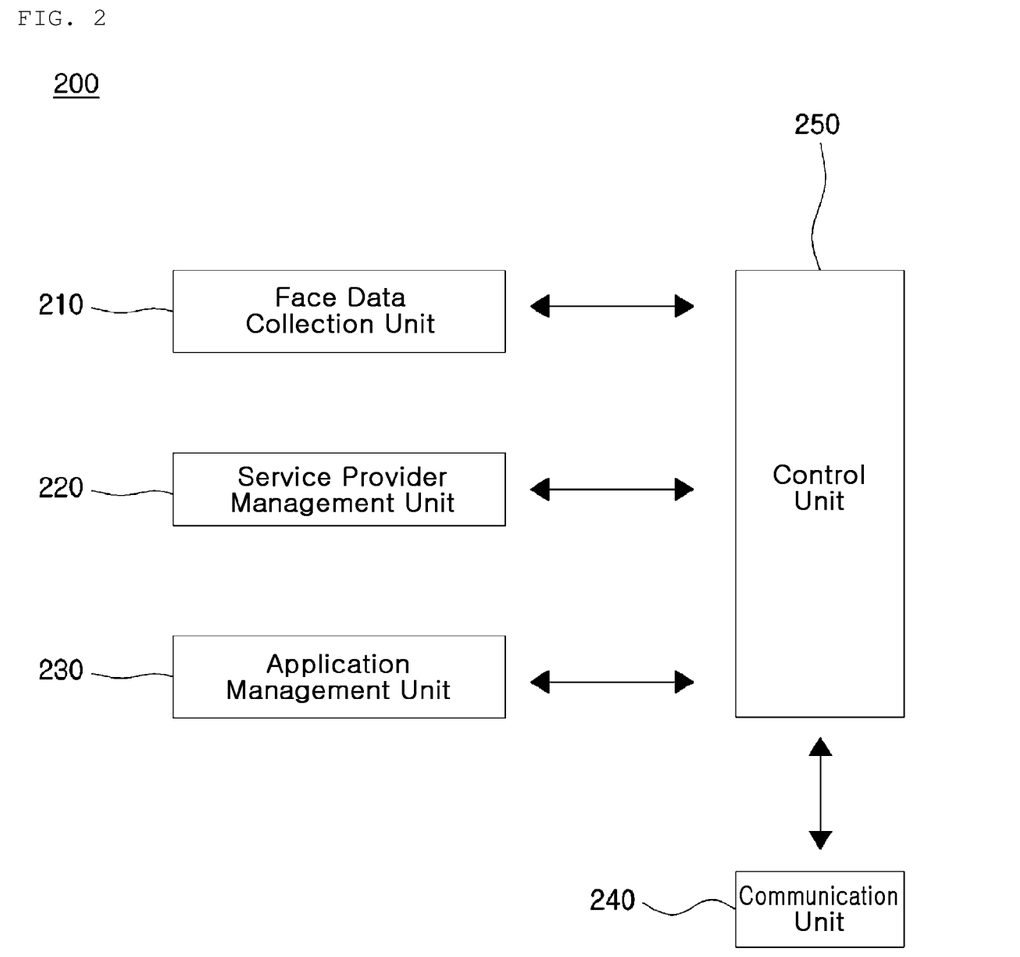
FIG. 2 specifically shows the internal configuration of a main system according to one embodiment of the invention.

Hereinafter, the internal configuration of the main system 200 according to the invention and the functions of the respective components thereof will be discussed.

FIG. 2 specifically shows the internal configuration of the main system 200 according to one embodiment of the invention.

As shown in FIG. 2, the main system 200 may comprise a face data collection unit 210, a service provider management unit 220, an application management unit 230, a communication unit 240, and a control unit 250. According to one embodiment of the invention, at least some of the face data collection unit 210, the service provider management unit 220, the application management unit 230, the communication unit 240, and the control unit 250 may be program modules to communicate with the user terminal device 300, the service provider server 400, or the face data generation device 500. The program modules may be included in the main system 200 in the form of operating systems, application program modules or other program modules, while they may be physically stored on a variety of commonly known storage devices. Further, the program modules may also be stored in a remote storage device that may communicate with the main system 200. Meanwhile, such program modules may include, but not limited to, routines, subroutines, programs, objects, components, data structures and the like for performing specific tasks or executing specific abstract data types as will be described below in accordance with the invention.

First, according to one embodiment of the invention, the face data collection unit 210 may function to collect face-related data including face data generated by the face data generation device 500, with respect to at least one user. Specifically, according to one embodiment of the invention, the face data may be generated by a facial bone scanning device or a facial image photographing device installed in a predetermined place. For example, the face data may include data on the size, proportion, position and the like of the entire face or each part thereof of the user, and an image of the entire face or each part thereof. Here, the image included in the face data may be a photographed actual image or a scanned and rendered virtual image, and may be two or three-dimensional.

Further, according to one embodiment of the invention, the face-related data may further include consultation data generated in association with the face data. Specifically, according to one embodiment of the invention, the consultation data may be automatically generated on the basis of the associated face data, or manually generated by an administrator (e.g., an expert such as a physician and a professional consultant).

Next, according to one embodiment of the invention, the service provider management unit 220 may function to determine a service provider matched with the face-related data of the user desiring to receive services, using a predetermined service provider commission algorithm.

Specifically, according to one embodiment of the invention, the service provider management unit 220 may search for the service provider matched with the face-related data of the user from among at least one service provider registered in a predetermined service provider pool. Further, according to one embodiment of the invention, the service provider pool may include providers of medical services (such as cosmetic surgery and dermatologic treatment), products (such as cosmetics and eyeglasses) and the like, and the providers may be stored in the service provider pool by categories. Meanwhile, according to one embodiment of the invention, the service provider pool may be organized at a request of a service provider or with an approval of an administrator of the main system 200.

Further, according to one embodiment of the invention, the service provider management unit 220 may function to transmit the face-related data of the user desiring to receive services to the server 400 of the service provider determined to be matched with the face-related data of the corresponding user. The transmitted face-related data may be utilized when the service provider provides face-based services to the corresponding user.

Furthermore, according to one embodiment of the invention, the service provider management unit 220 may function to receive, from the server 400 of the service provider, the face-related data changed or newly generated by the services provided from the service provider to the user. For example, it may be assumed that a user undergoes cosmetic surgery in a hospital, which is a service provider. In this case, the face data of the user may be changed or newly generated as the face of the user is changed due to the cosmetic surgery. The service provider management unit 200 according to one embodiment of the invention may receive the face-related data changed or newly generated as above from the server 400 of the corresponding service provider.

Next, according to one embodiment of the invention, the application management unit 230 may function to manage an application for assisting a user to receive information on data processed or operations performed by the face data collection unit 210 and the service provider management unit 220 as mentioned above (i.e., information on the face-based services) through the terminal device 300 of the user.

Specifically, according to one embodiment of the invention, the user may receive, through the application installed in the user terminal device 300, information on the face-related data of the user, information on the service provider determined to be matched with the face-related data of the user, information on the face-related data of the user changed or newly generated by the service provider, and the like.

Figure 3:
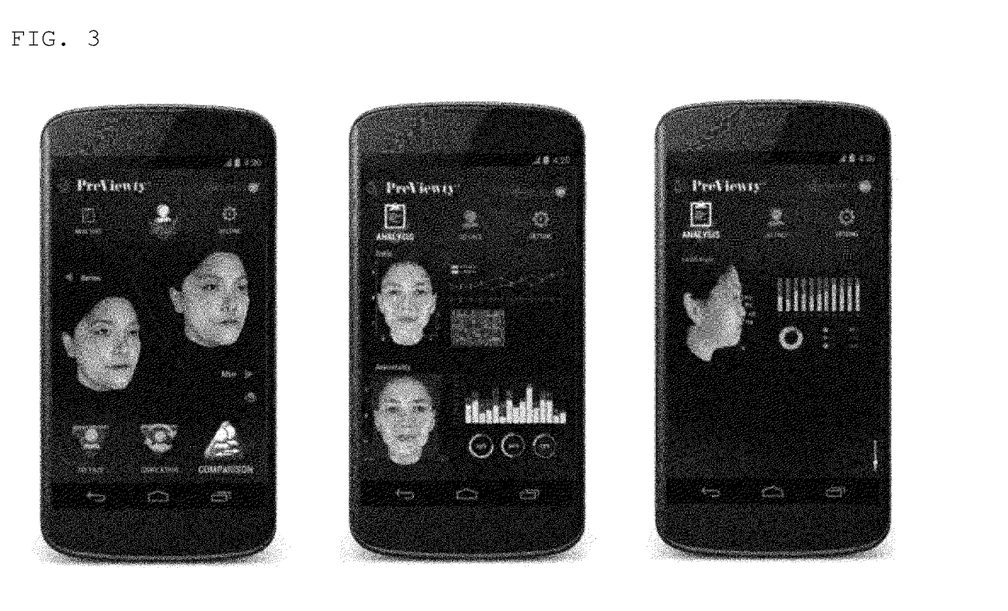
FIG. 3 illustratively shows pictures in which information on face-based services is provided through an application (called "Previewty") according to one embodiment of the invention.

FIG. 3 illustratively shows pictures in which information on face-based services is provided through an application (called "Previewty") according to one embodiment of the invention.

Further, according to one embodiment of the invention, the application management unit 230 may function to manage an application for assisting a user to receive additional information relevant to the face-related data of the user, or relevant to the service provider determined to be matched with the face-related data of the user. For example, the additional information may include advertisement information for promoting services or products relevant to the face-related data of the user, wayfinding information necessary for traveling from a current location of the user to a store location of the service provider, and the like.

Figure 4:
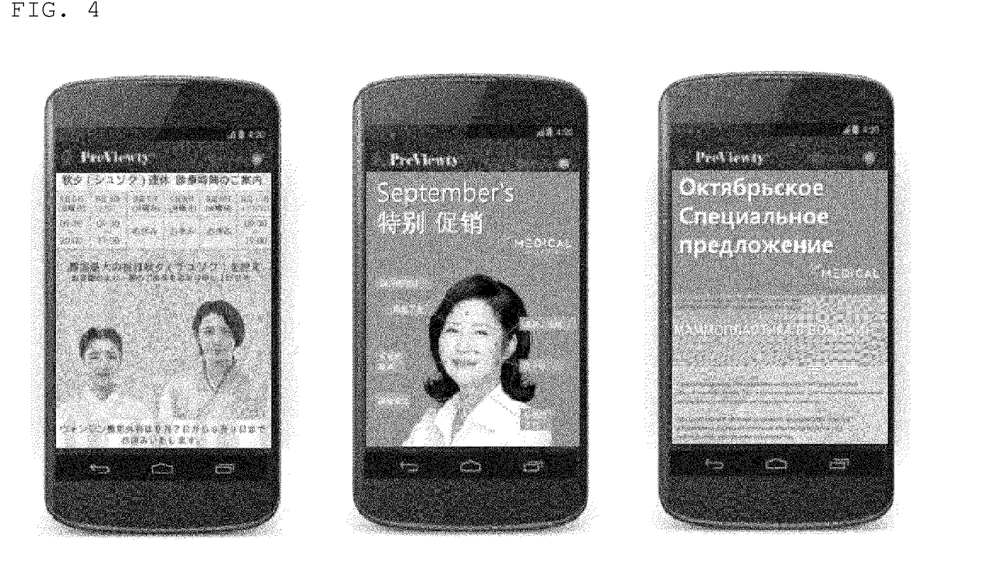
FIG. 4 illustratively shows pictures in which a variety of additional information is provided through an application (called "Previewty") according to one embodiment of the invention.

FIG. 4 illustratively shows pictures in which a variety of additional information is provided through an application (called "Previewty") according to one embodiment of the invention.

Figure 5:
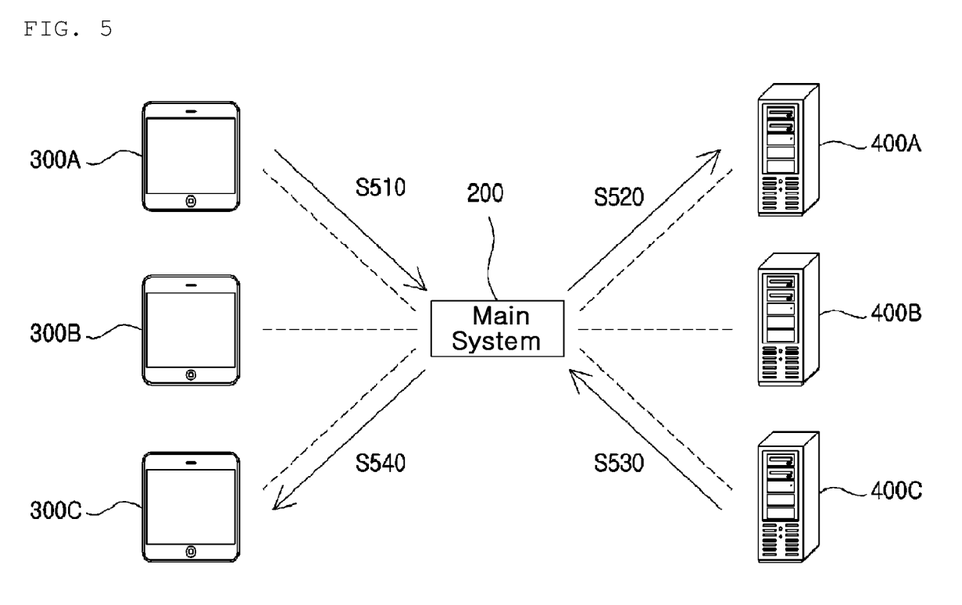
FIG. 5 illustratively shows how push information is transferred according to one embodiment of the invention.

Meanwhile, FIG. 5 illustratively shows how push information is transferred according to one embodiment of the invention.

Referring to FIG. 5, according to one embodiment of the invention, the main system 200 may function to transfer push information received from a user terminal device 300A to a server 400A of a corresponding service provider (S510, S520), and conversely, to transfer push information received from a server 400C of a service provider to a user terminal device 300C of a corresponding user (S530, S540). Here, the transfer of push information may be performed by an application managed by the main system 200.

Further, according to one embodiment of the invention, the main system 200 may store (i.e., back up) the push information transferred between the user terminal device 300 and the service provider server 400 in a predetermined database (not shown), so that the push information may be normally transferred even when one of the user terminal device 300 and the service provider server 400 is not connected to the main system 200.

For example, according to one embodiment of the invention, the push information transferred between the user terminal device 300 and the service provider server 400 may include information on face-related data inputted from a diagnosis or treatment device (not shown) of a hospital connected to the service provider server 400, or information such as notification inputted from an administrator terminal device (not shown) connected to the service provider server 400.

Next, the communication unit 240 according to one embodiment of the invention may function to enable data transmission/reception from/to the main system 200.

Lastly, the control unit 250 according to one embodiment of the invention may function to control data flow among the face data collection unit 210, the service provider management unit 220, the application management unit 230, and the communication unit 240. That is, the control unit 250 according to the invention may control data flow into/out of the main system 200 or data flow among the respective components of the main system 200, such that the face data collection unit 210, the service provider management unit 220, the application management unit 230, and the communication unit 240 may carry out their particular functions, respectively.

The embodiments according to the invention as described above may be implemented in the form of program instructions that can be executed by various computer components, and may be stored on a non-transitory computer-readable recording medium. The computer-readable recording medium may include program instructions, data files, data structures and the like, separately or in combination. The program instructions stored on the computer-readable recording medium may be specially designed and configured for the present invention, or may also be known and available to those skilled in the computer software field. Examples of the computer-readable recording medium include the following: magnetic media such as hard disks, floppy disks and magnetic tapes; optical media such as compact disk-read only memory (CD-ROM) and digital versatile disks (DVDs); magneto-optical media such as floptical disks; and hardware devices such as read-only memory (ROM), random access memory (RAM) and flash memory, which are specially configured to store and execute program instructions. Examples of the program instructions include not only machine language codes created by a compiler or the like, but also high-level language codes that can be executed by a computer using an interpreter or the like. The above hardware devices may be changed to one or more software modules to perform the processes of the present invention, and vice versa.

Although the present invention has been described in terms of specific items such as detailed elements as well as the limited embodiments and the drawings, they are only provided to help more general understanding of the invention, and the present invention is not limited to the above embodiments. It will be appreciated by those skilled in the art to which the present invention pertains that various modifications and changes may be made from the above description.

Therefore, the spirit of the present invention shall not be limited to the above-described embodiments, and the entire scope of the appended claims and their equivalents will fall within the scope and spirit of the invention.

What is claimed is:

1. A method performed in a system for providing face-based services, the system comprising a face data generation device and a main system, and the method comprising the steps of:
   (a) generating, by the face data generation device, face data to be included in face-related data, with respect to at least one user;
   (b) determining, by the main system, a service provider matched with the face-related data of a first user desiring to receive services, using a service provider commission algorithm;
   (c) collecting and transmitting, by the main system, the face-related data of the first user to a server of the determined service provider;
   (d) receiving, by the main system, from the server of the determined service provider, the face-related data changed in response to a face of the first user being changed by the services provided from the service provider to the face of the first user;
   (e) determining, by the main system, another service provider matched with the changed face-related data, using the service provider commission algorithm; and
   (f) transmitting, by the main system, the changed face-related data or information on the another service provider to a terminal of the first user,
   wherein information on data processed in at least one of steps (a), (b), (c) and (d), or information on operations performed in at least one of steps (a), (b), (c) and (d), is provided to the terminal device of the first user,
   wherein the face data include data on a size, a proportion, a position of an entire face or each part thereof of the at least one user, and an image of the entire face or each part thereof of the at least one user, and
   wherein the matching is performed by searching for the service provider from among at least one service provider registered in a predetermined service provider pool, on the basis of the face-related data of the first user, the services that the first user desires to receive, and a category of the at least one registered provider.

2. The method of claim 1, wherein the face data generation device is a facial bone scanning device or a facial image photographing device.

3. The method of claim 1, wherein the face-related data further include consultation data generated in association with the face data.

4. The method of claim 1, wherein the service provider includes at least one of a provider of medical services, a provider of cosmetic-related services, a provider of eyeglass-related services, and a provider of accessory-related services.

5. The method of claim 1, wherein additional information corresponding to the data processed in at least one of steps (a), (b), (c) and (d) is transmitted to the terminal device of the first user.

6. The method of claim 1, wherein push information received from a terminal device of a user, or from a server of a service provider, is transmitted to a server of a service provider corresponding to the push information, or to a terminal device of a user corresponding to the push information.

7. The method of claim 6, wherein the push information includes the changed face-related data.

8. The method of claim 1, wherein the services include cosmetic surgery or dermatologic treatment, and the face-related data is changed by the cosmetic surgery or the dermatologic treatment.

9. A non-transitory computer-readable recording medium having stored thereon a computer program for executing a method performed in a system comprising a face data generation device and a main system, and the method comprising the steps of:
   (a) generating, by the face data generation device, face data to be included in face-related data, with respect to at least one user;

(b) determining, by the main system, a service provider matched with the face-related data of a first user desiring to receive services, using a service provider commission algorithm;

(c) collecting and transmitting, by the main system, the face-related data of the first user to a server of the determined service provider;

(d) receiving, by the main system, from the server of the determined service provider, the face-related data changed in response to a face of the first user being changed by the services provided from the service provider to the face of the first user;

(e) determining, by the main system, another service provider matched with the changed face-related data, using the service provider commission algorithm; and (f) transmitting, by the main system, the changed face-related data or information on the another service provider to a terminal of the first user, wherein information on data processed in at least one of steps (a), (b), (c) and (d), or information on operations performed in at least one of steps (a), (b), (c) and (d), is provided to the terminal device of the first user, wherein the face data include data on a size, a proportion, a position of an entire face or each part thereof of the at least one user, and an image of the entire face or each part thereof of the at least one user, and wherein the matching is performed by searching for the service provider from among at least one service provider registered in a predetermined service provider pool, on the basis of the face-related data of the first user, the services that the first user desires to receive, and a category of the at least one registered provider.

10. The non-transitory computer-readable recording medium of claim 9, wherein the face data generation device is a facial bone scanning device or a facial image photographing device.

11. The non-transitory computer-readable recording medium of claim 9, wherein the face-related data further include consultation data generated in association with the face data.

12. The non-transitory computer-readable recording medium of claim 9, wherein the service provider includes at least one of a provider of medical services, a provider of cosmetic-related services, a provider of eyeglass-related services, and a provider of accessory-related services.

13. The non-transitory computer-readable recording medium of claim 9, wherein additional information corresponding to the data processed in at least one of steps (a), (b), (c) and (d) is transmitted to the terminal device of the first user.

14. The non-transitory computer-readable recording medium of claim 9, wherein push information received from a terminal device of a user, or from a server of a service provider, is transmitted to a server of a service provider corresponding to the push information, or to a terminal device of a user corresponding to the push information.

15. The non-transitory computer-readable recording medium of claim 14, wherein the push information includes the changed face-related data.

16. The non-transitory computer-readable recording medium of claim 9, wherein the services include cosmetic surgery or dermatologic treatment, and the face-related data is changed by the cosmetic surgery or the dermatologic treatment.

17. A system for providing face-based services, comprising:

a face data generation device configured to generate face data to be included in face-related data, with respect to at least one user; and a main system comprising:

a processor; and a memory comprising program modules, when executed by the processor, causing the main system to:

determine a service provider matched with the face-related data of a first user desiring to receive services, using a service provider commission algorithm, to collect and transmit the face-related data of the first user to a server of the determined service provider, to receive, from the server of the determined service provider, the face-related data changed in response to a face of the first user being changed by the services provided from the service provider to the face of the first user, and to determine another service provider matched with the changed face-related data, using the service provider commission algorithm; and provide information on data processed by the face data generation device and the main system, or information on operations performed by the face data generation device and the main system, to a terminal device of the first user, and to transmit the changed face-related data or information on the another service provider to the terminal of the first user, wherein the face data include data on a size, a proportion, a position of an entire face or each part thereof of the at least one user, and an image of the entire face or each part thereof of the at least one user, and wherein the matching is performed by searching for the service provider from among at least one service provider registered in a predetermined service provider pool, on the basis of the face-related data of the first user, the services that the first user desires to receive, and a category of the at least one registered provider.

18. The system of claim 17, wherein the services include cosmetic surgery or dermatologic treatment, and the face-related data is changed by the cosmetic surgery or the dermatologic treatment.

19. The system of claim 17, wherein the face data generation device is a facial bone scanning device or a facial image photographing device.

20. The system of claim 17, wherein push information received from a terminal device of a user, or from a server of a service provider, is transmitted to a server of a service provider corresponding to the push information, or to a terminal device of a user corresponding to the push information, and wherein the push information includes the changed face-related data.

* * * * *